(12) United States Patent
Yu et al.

(10) Patent No.: US 11,726,016 B2
(45) Date of Patent: Aug. 15, 2023

(54) BIONIC ORAL CAVITY STRUCTURE FOR TESTING AND APPLICATION THEREOF

(71) Applicant: JIANGNAN UNIVERSITY, Jiangsu (CN)

(72) Inventors: Jinghu Yu, Jiangsu (CN); Shu Cao, Jiangsu (CN); Shanhua Qian, Jiangsu (CN); Yi Cao, Jiangsu (CN); Xingyu Zhou, Jiangsu (CN); Hao Yu, Jiangsu (CN)

(73) Assignee: JIANGNAN UNIVERSITY, Jiangsu (CN)

( * ) Notice: Subject to any disclaimer, the term of this patent is extended or adjusted under 35 U.S.C. 154(b) by 403 days.

(21) Appl. No.: 17/123,074

(22) Filed: Dec. 15, 2020

(65) Prior Publication Data

US 2021/0102877 A1    Apr. 8, 2021

Related U.S. Application Data

(63) Continuation of application No. PCT/CN2019/114298, filed on Oct. 30, 2019.

(51) Int. Cl.
  *G01N 3/32*  (2006.01)
  *A61C 19/04*  (2006.01)
  *A61C 13/00*  (2006.01)
  *G01N 3/02*  (2006.01)

(52) U.S. Cl.
  CPC .............. *G01N 3/02* (2013.01); *G01N 3/32* (2013.01); *A61C 13/00* (2013.01); *G01N 2203/0073* (2013.01)

(58) Field of Classification Search
  CPC .. G01N 3/02; G01N 3/32; G01N 3/40; G01N 2203/0073; G01N 33/02; G01N 11/14; G09B 23/283; A61C 7/008; A61C 19/04; A61C 1/084; A61C 8/0053; A61C 19/05; A61C 8/0018; A61C 8/0089; A61C 7/08; A61C 7/10; A61C 8/0022; A61C 7/00; A61C 8/0048; A61C 13/0004; A61B 5/4836; A61F 5/566
  See application file for complete search history.

(56) References Cited

U.S. PATENT DOCUMENTS

| | | | | |
|---|---|---|---|---|
| 4,468,198 A * | 8/1984 | Kataoka | ............... | A61C 19/045 433/64 |
| 5,743,732 A * | 4/1998 | Watson | .................. | A61C 19/04 433/56 |
| 6,120,290 A * | 9/2000 | Fukushima | ............ | A61C 11/00 433/64 |
| 8,021,149 B2 * | 9/2011 | Gutman | ................. | A61C 11/00 433/68 |

\* cited by examiner

*Primary Examiner* — Brandi N Hopkins

(57) ABSTRACT

A bionic oral cavity structure for testing and application thereof are provided for solving a technical problem that actual test process of the conventional bionic oral cavity structure needs to be improved. The bionic oral cavity structure for testing includes: an upper jaw, a lower jaw, a drive unit, a sensor and a controller, wherein a gum is made of a soft elastic material, and a base of the gum has a through-hole; a cap is formed by extending upward from a top opening of the through-hole; the tooth comprises a molar made of a hard material, and an implant; a top end of the implant passes through the through-hole of the gum and then extends into the cap; the gum and the implant are detachably mounted on the mounting plate; the sensor is a flexible sensor which covers the cap.

10 Claims, 4 Drawing Sheets

BIONIC ORAL CAVITY STRUCTURE FOR TESTING AND APPLICATION THEREOF

CROSS REFERENCE OF RELATED APPLICATION

The application is a continuation application of a PCT application No. PCT/CN2019/114298, fled on Oct. 30, 2019; and claims the priority of Chinese Patent Application No. CN 201910859493.7, filed to the China National Intellectual Property Administration (CNIPA) on Sep. 11, 2019, the entire content of which are incorporated hereby by reference.

BACKGROUND OF THE PRESENT INVENTION

Field of Invention

The present invention relates to a technical field of bionic machinery, and more particularly to a bionic oral cavity structure for testing and application thereof.

Description of Related Arts

Conventional bionic oral cavity structure includes upper teeth, lower teeth and corresponding sensors. The upper teeth are installed on an upper part of a frame. The lower teeth are fixed in a cavity of a container and located below the upper teeth. The container is fixed on a movable platform, and a top portion of the container has an opening. A mastication drive device is connected to the movable platform, which is used to lift the movable platform so that the lower teeth move towards the upper teeth. With different drive control, movements such as up-down bite, left-right grinding, and cutting-off with front teeth can be achieved, thereby providing the bionic chewing.

Although the conventional bionic oral cavity structure has achieved the purpose of bionic chewing, actual test process thereof needs to be improved. Chinese patent application CN201010255196.0 disclosed biomimetic detection robot for testing physical properties of food. The robot also has a biomimetic oral cavity structure, wherein pressure sensors are set on surfaces of the upper and lower teeth to collect force data of the teeth on the food, so as to reflect the physical properties of the food at different levels of chewing. However, conventional pressure sensor has a large volume, which will affect the surface structure of the tooth when installed on the surface of the tooth, thereby affecting the purpose of bionic chewing. Furthermore, when detecting fatigue strength of denture, the pressure sensor generally realizes the corresponding detection through tooth deformation. However, the denture has high strength and small deformation, which makes it difficult to accurately detect.

SUMMARY OF THE PRESENT INVENTION

An object of the present invention is to provide a bionic oral cavity structure for testing and application thereof, thereby solving a technical problem that actual test process of the conventional bionic oral cavity structure needs to be improved.

Accordingly, in order to accomplish the above objects, the present invention provides a bionic oral cavity structure for testing, comprising: an upper jaw, a lower jaw, a drive unit, a sensor and a controller, wherein each of the upper jaw and the lower jaw comprises a tooth, a gum and a mounting plate; the tooth, the gum, and the mounting plate of the upper jaw are mounted on a static platform, and the static platform is mounted on a frame; the tooth, the gum, and the mounting plate of the lower jaw are installed on a movable platform, and the movable platform is connected to the drive unit, thereby moving up and down as well as left and right; the drive unit and the sensor are both electrically connected to the controller; wherein:

the gum is made of a soft elastic material, and a base of the gum has a through-hole drilled from top to bottom; a cap is formed by extending upward from a top opening of the through-hole; the tooth comprises a molar made of a hard material, and an implant; a top end of the implant passes through the through-hole of the gum and then extends into the cap; the gum and the implant are detachably mounted on the mounting plate; the sensor is a flexible sensor which covers the cap; the flexible sensor is provided with at least one sensing unit corresponding to a top portion of the cap and with at least two sensing units evenly distributed around a side portion of the cap; a bottom portion of the molar has a counterbore, and the molar is mounted on the gum; a structure constituted by the flexible sensor, the cap and the top end of the implant is integrally embedded in and tightly cooperate with the counterbore; the molar, the flexible sensor, the cap and the implant are arranged in sequence with no gap.

Preferably, the gum is made of silica gel; in a non-testing state, the cap tightly cooperates with the molar and is in an elastic compression state; when an external force is applied, the cap is further compressed.

Preferably, in a non-testing state, an internal side wall and a top wall of the counterbore are tightly attached to a non-sensing end of the flexible sensor; an external side wall and a top wall of the cap are tightly attached to a sensing end of the flexible sensor; and an internal side wall and an internal top wall of the cap are tightly attached to an external side wall and an external top wall of the top end of the implant.

Preferably, the tooth of the upper jaw and the tooth of the lower jaw correspond to each other, and each of the upper jaw and the lower jaw is provided with an eddy current sensor; the eddy current sensor of the upper jaw part is installed directly above the implant with a certain gap, and the eddy current sensor of the lower jaw is installed directly below the implant with a certain gap.

Preferably, three pairs of the drive units are evenly distributed around the movable platform; each of the drive units comprises a motor, a screw rod, a screw nut, a sliding block, a guide post, a connecting rod and a spherical hinge, wherein an output end of the motor is connected to the screw rod; two ends of the screw rod and the guide post are respectively supported on a support plate and are all arranged along a vertical direction; the screw nut is matched with the screw rod and fixedly connected to the sliding block; the sliding block cooperates with the guide post; two ends of the connecting rod are connected to the sliding block and the movable platform respectively through the spherical hinge; the motor and the support plate are mounted on the frame.

Preferably, the implant is screwed with the mounting plate and fastened by a nut.

Preferably, a bottom end surface of the base is attached to the mounting plate, and the implant penetrates the mounting plate and the base from bottom to top.

Preferably, the lower jaw is provided with a tongue, and the tongue is made of silica gel and mounted on the mounting plate.

The present invention also provides a method for testing physical properties of food comprising using the above bionic oral cavity structure.

The present invention also provides a method for testing denture fatigue comprising using the above bionic oral cavity structure.

Beneficial effects of the bionic oral cavity structure of the present invention are as follows:

(1) The sensor and the gum are both flexible. The gum is further provided with a cap covering the top end of the implant. The flexible sensor is arranged between the counterbore of the molar and the cap. At the same time, the molar, the flexible sensor, the cap, and the implant are sequentially arranged in close contact with each other. After the upper and lower teeth squeezes or/and shear the food, force is transmitted from the molar and the flexible sensor to the cap of the gum. The cap and the gum are integrated and both are made of soft elastic materials, while the molar outside the cap and the implant inside the cap are both made of hard materials. Therefore, during force transmission, obvious elastic deformation of the cap will occur. This obvious elastic deformation can be more easily detected by the flexible sensor and can be converted into load changes needed.

(2) The flexible sensor is placed between the counterbore of the molar and the cap of the gum, which will not contact or rub with food. On one hand, it avoids affecting the bionic chewing. On the other hand, it ensures the service life of the flexible sensor.

(3) In food texture testing experiments, different chewing methods should be applied to food materials, such as squeezing caused by up-down biting, and shearing caused by left-right grinding. The flexible sensor covering the cap can simultaneously detect forces in different directions generated by squeezing and shearing. Specifically, when the top of the cap is further compressed during the up-down biting, a top covering portion of the flexible sensor can feedback a force in an up-down direction. After a side portion of the cap is further compressed during the left-right grinding, the top covering portion of the flexible sensor can feedback a force in a left-right direction. At the same time, the forces are directly fed back from the flexible sensor of each tooth in contact with the food, which means each detected load is closer to a real load of a single tooth. Therefore, the testing method is more in line with bionic design.

(4) In the denture fatigue testing experiment, the implant of each tooth at different positions needs to be tested separately. In the bionic oral cavity structure of the present invention, the implant, the mounting plate, and the gum are detachably connected, which is conducive to replacing and detecting the implant of each tooth at different positions. Stress thresholds and fracture detection of the implant are fed back by the flexible sensor. Displacements generated after the implant is loosened are fed back by the metal eddy current sensor. Force feedback and displacement feedback are used to accurately determining the stress threshold, fracture and damage of molar, making the detection more accurate.

DETAILED DESCRIPTION OF THE PREFERRED EMBODIMENT

Figure 1:
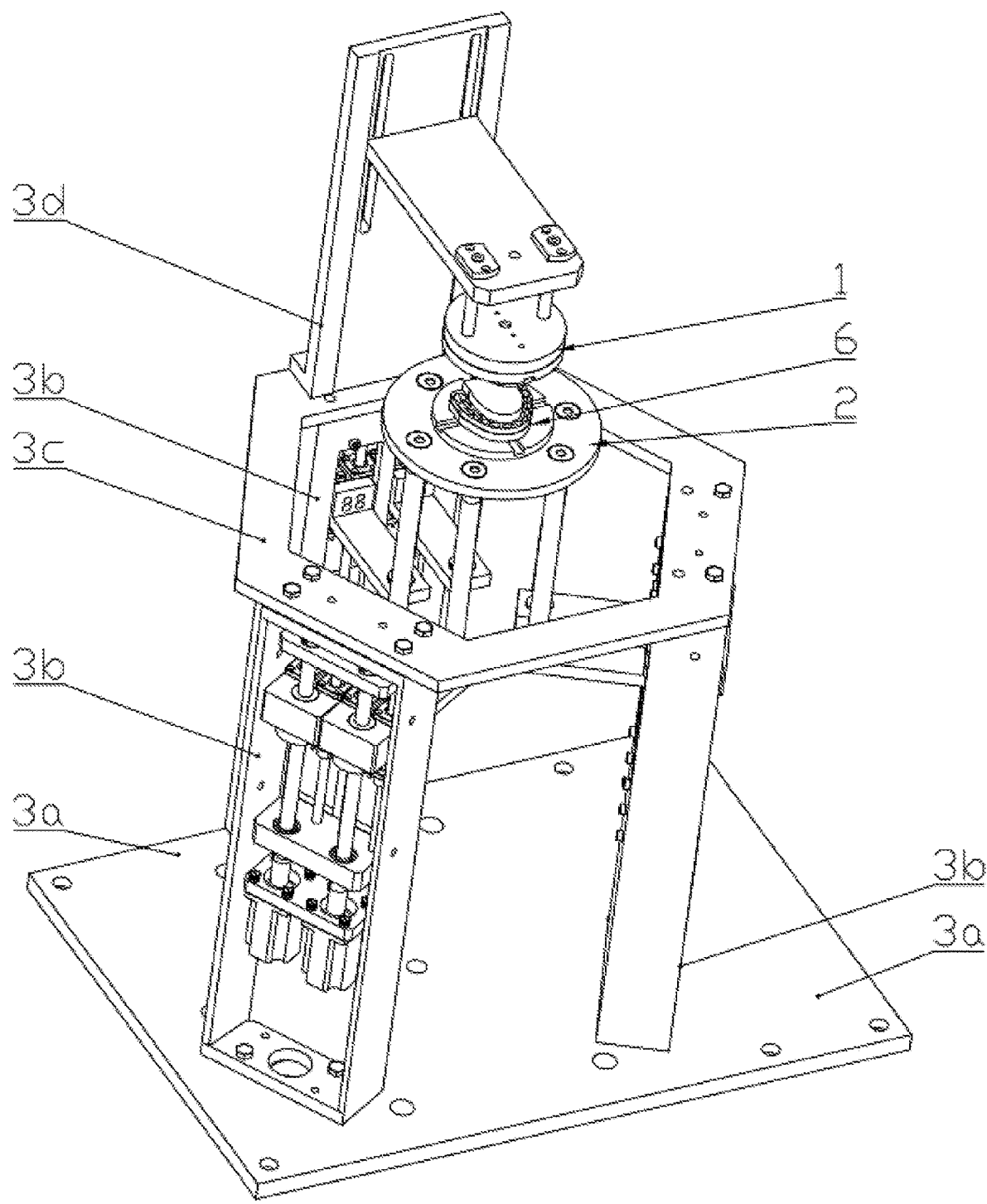
FIG. 1 is a perspective view of a bionic oral cavity structure of the present invention.
Figure 2:
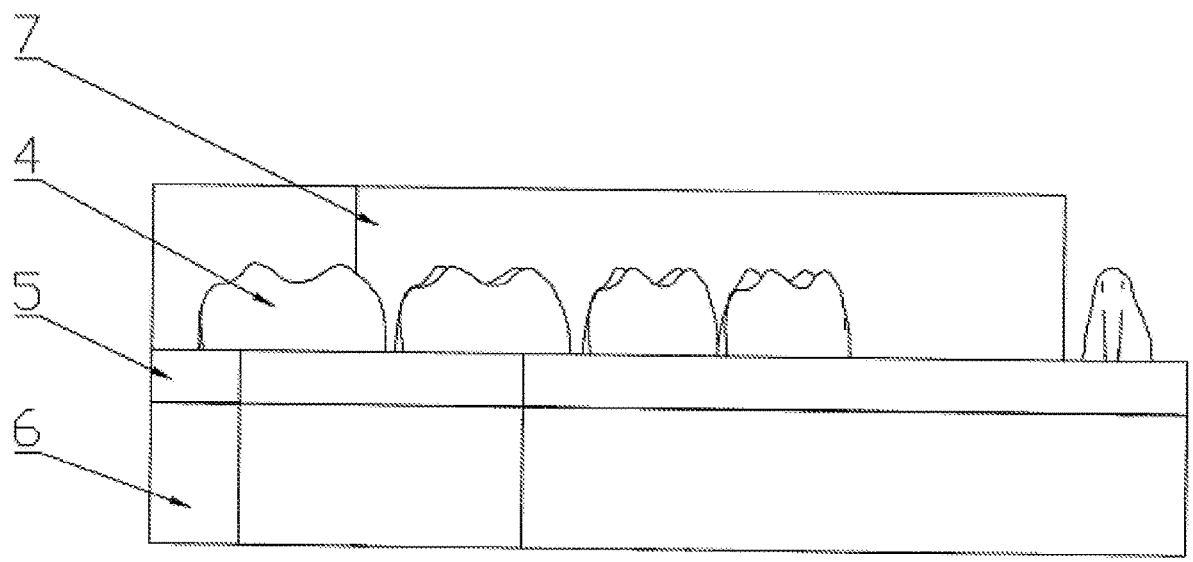
FIG. 2 illustrate a structure of a lower jaw of the present invention, wherein some teeth are not installed.
Figure 3:
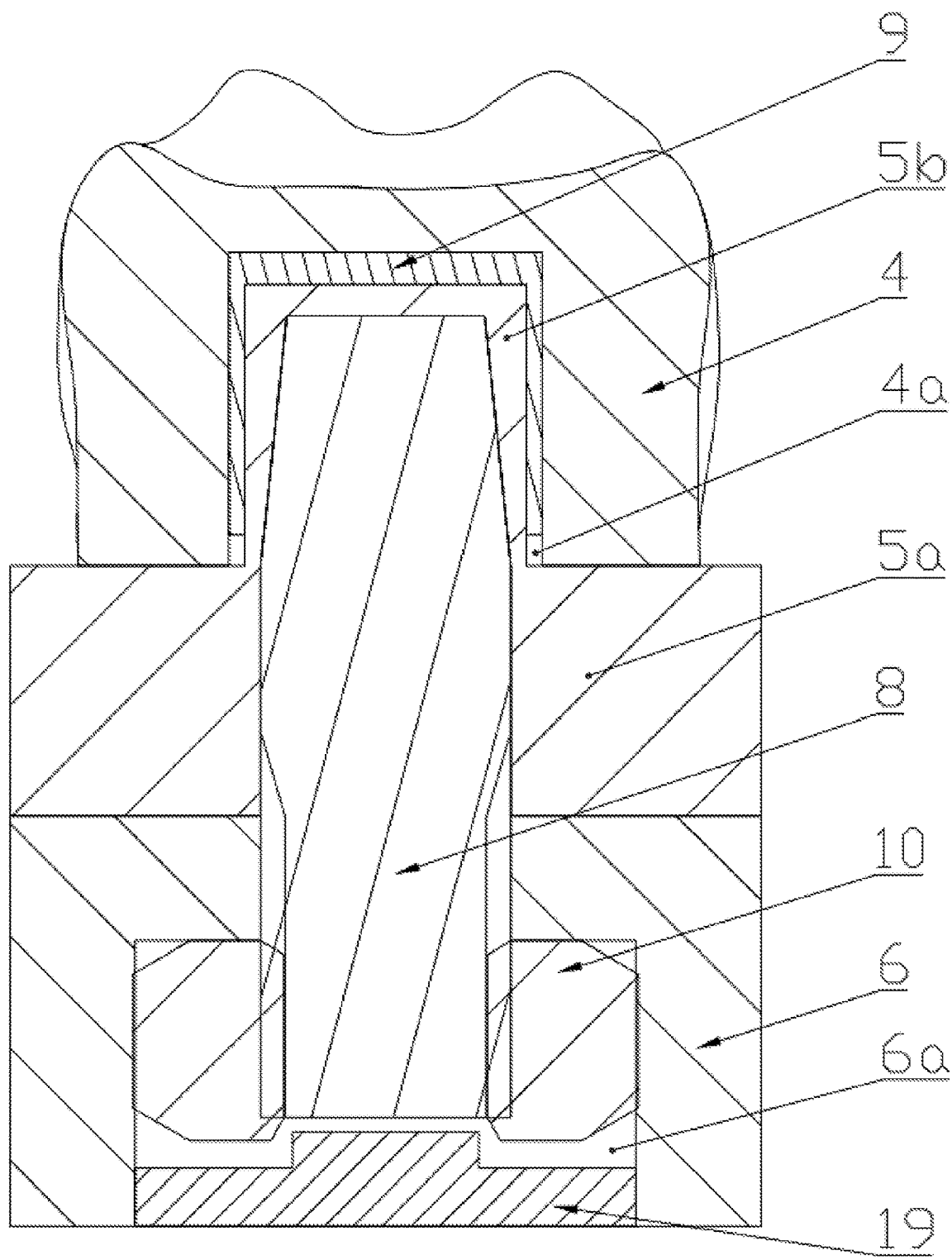
FIG. 3 is a cross-sectional view of a tooth, a gum and a mounting plate of the present invention.
Figure 4:
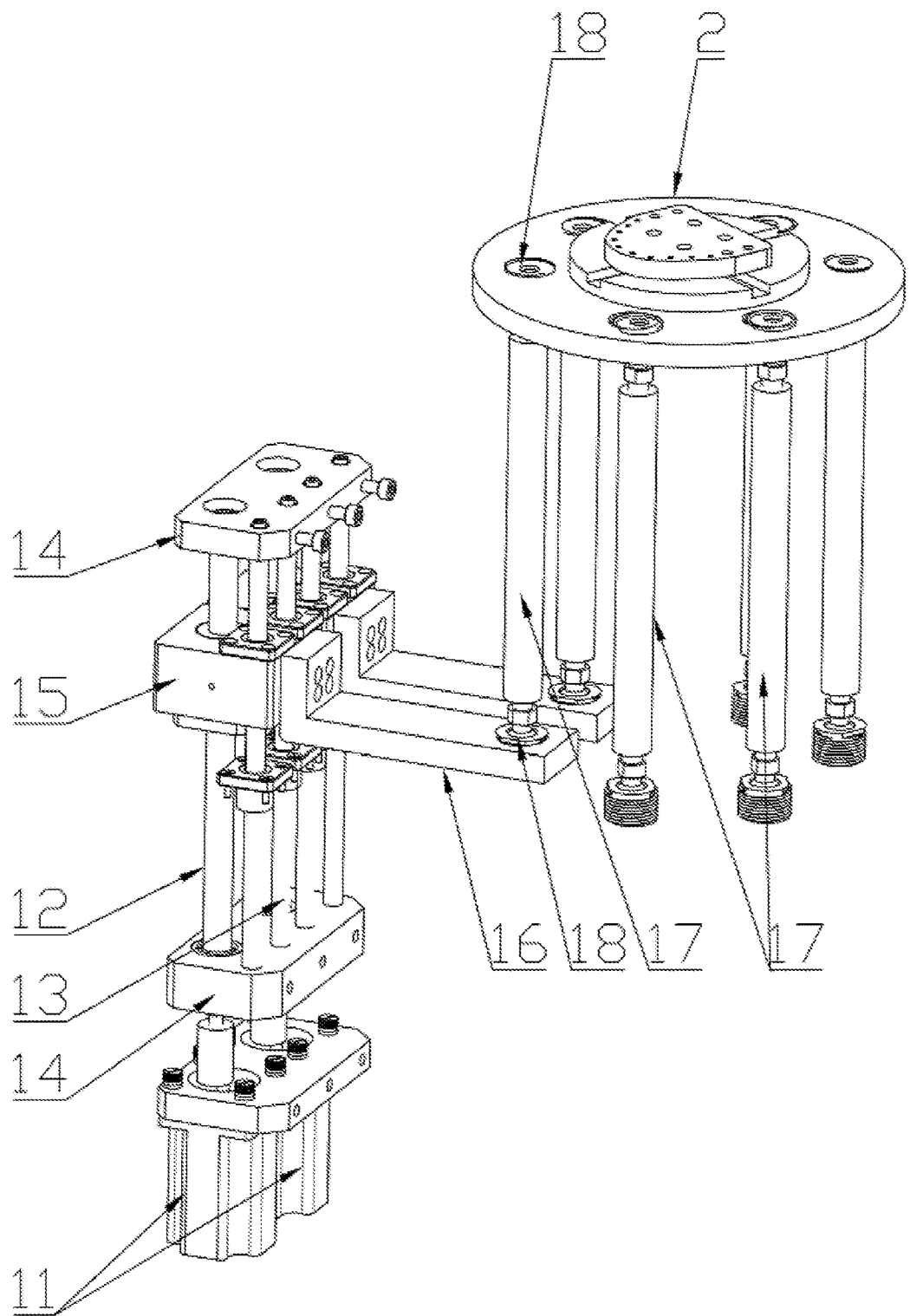
FIG. 4 is a perspective view of a drive unit of the present invention.

Referring to FIGS. 1-4, the present invention provides a bionic oral cavity structure for testing, comprising: an upper jaw, a lower jaw, a drive unit, a sensor and a controller, wherein each of the upper jaw and the lower jaw comprises a tooth 4, a gum 5 and a mounting plate 6; the lower jaw is also provided with a tongue 7; the tooth 4, the gum 5 (i.e. the upper tooth and the upper gum), and the mounting plate 6 of the upper jaw are mounted on a static platform 1, and the static platform 1 is mounted on a mounting base 3d of a frame; the tooth 4, the gum 5 (i.e. the lower tooth and the lower gum), and the mounting plate 6 of the lower jaw are installed on a movable platform 2; the tongue 7 is made of silica gel and is mounted on the mounting plate 6 of the lower jaw; the movable platform 2 is connected to the drive unit, thereby moving up and down as well as left and right; the drive unit and the sensor are both electrically connected to the controller;

the tooth 4 comprises a molar made of a hard material, and an implant 8; a bottom of the implant 8 is screwed with the mounting plate 6 and fastened by a nut 10; a top end of the implant 8 passes through a through-hole of the gum 5 and then extends into a cap 5b; the gum 5 and the implant 8 are detachably mounted on the mounting plate 6; the sensor is a flexible sensor 9 which covers the cap 5b; the flexible sensor is provided with at least one sensing unit corresponding to a top portion of the cap 5b and with at least two sensing units evenly distributed around a side portion of the cap 5b; a bottom portion of the molar has a counterbore 4a, and the molar is mounted on the gum 5; a structure constituted by the flexible sensor 9, the cap 5b and the top end of the implant 8 is integrally embedded in and tightly cooperate with the counterbore 4a; in a non-testing state, the cap 5b tightly cooperates with the molar and is in an elastic compression state; when an external force is applied, the cap is further compressed; the molar, the flexible sensor 9, the cap 5b and the implant 8 are arranged in sequence with no gap; specifically, an internal side wall and a top wall of the counterbore 4a are tightly attached to a non-sensing end (i.e. an external side wall and an external top wall) of the flexible sensor; an external side wall and a top wall of the cap 5b are tightly attached to a sensing end (i.e. an internal side wall and an internal top wall) of the flexible sensor; and an internal side wall and an internal top wall of the cap 5b are tightly attached to an external side wall and an external top wall of the top end of the implant 8.

Three pairs of the drive units are evenly distributed around the movable platform 2; each of the drive units comprises a motor 11, a screw rod 12, a screw nut, a sliding block 15, a guide post 13, a connecting rod 17 and a spherical hinge 18, wherein an output end of the motor 11 is connected to the screw rod 12; two ends of the screw rod 12 and two ends of the guide post 13 are respectively supported on a support plate 14 and are all arranged along a vertical direction; the screw nut is matched with the screw rod 12 and fixedly connected to the sliding block 15; the sliding block 15 cooperates with the guide post 13; two ends of the connecting rod 17 are connected to a supporting base 16 mounted on a side of the sliding block and the movable platform 2 respectively through the spherical hinge 18; the motor 11 and the support plate 14 are mounted on a bottom mounting frame 3b of the frame. The 3 pairs of the drive units, namely 6 drive units, can realize six degrees of freedom movement of the movable platform, thereby simulating of lower jaw movement of human during chewing. The drive units also cooperate with the upper jaw installed on the static platform to simulate the complete oral cavity as well as biting and grinding movement of human.

The frame comprises a bottom plate 3a, wherein the bottom mounting frames 3b corresponding to the three pairs of the drive units are mounted on the bottom plate 3a; top ends of the bottom mounting frames 3b are connected by a ring-shaped connecting plate 3c, and a top mounting base 3d is fixed on the connecting plate 3c.

In the above embodiment, a portion of the flexible sensor 9, which covers top and side portions of the cap, is integrally formed. Or a split structure can be used, which means a first flexible sensor covers the top portion of the cap, and a second flexible sensor covers the side portion of the cap.

When the above-mentioned bionic oral cavity structure is used to detect physical properties of food, the sensor records deformation, force and time data of the food in a process of being chewed. A stress-time curve is drawn, wherein time is indicated in abscissa and stress is indicated in ordinate; detection values of a pressure sensor are positive, and detection value of a tension sensor are negative. A deformation-time curve is also drawn, wherein time is indicated in abscissa and deformation is indicated in ordinate. A stress-deformation curve is also drawn, wherein deformation is indicated in abscissa and stress is indicated in ordinate. According to these curves, related physical property data are detected as follows.

Bite strength (hardness): which is indicated by a force corresponding to a maximum peak value on the stress-time curve. The larger the value, the harder the food and the stronger the bite strength.

Adhesiveness: which is indicated by an inverted peak area below the abscissa on the stress-time curve. The greater an absolute value thereof, the stronger the adhesiveness of the food and the stickier taste of the food.

Elasticity (breaking force): which is indicated by a product of a force corresponding to a maximum peak value on the stress-deformation curve and a stretching distance. The larger the value, the longer the stretching distance and the better the elasticity of the food.

Extensibility (stretching time): which is indicated by a period from stretching the food to breaking of the food on the deformation-time curve. The larger the value, the better the extensibility.

Toughness: which is indicated by a product of a shearing force and a shearing distance on the stress-deformation curve when the food is sheared by chewing, namely a work done during shearing. The larger the value, the better the toughness.

Maximum shearing force: which is indicated by a force corresponding to a maximum peak value on the stress-deformation curve. The greater the value, the greater the force used to shear the food. The above bionic cavity structure can be used for testing denture fatigue.

To detect the fatigue strength of the implant with the above-mentioned bionic oral cavity structure, it is also necessary to load an eddy current sensor 19 for each tooth. For example, the eddy current sensor 19 is connected to the counterbore 6a of the mounting plate of the lower jaw through an interference fit (or directly fixed and installed on the movable platform and extends into the counterbore 6a). A probe position of the eddy current sensor 19 should be adjusted so that it faces the bottom end of the implant in a non-forced or non-testing state, wherein a distance between the eddy current sensor 19 and the bottom end of the implant is about 1 mm. Installation of the eddy current sensor of the upper jaw is opposite to that of the lower jaw, which means the eddy current is installed above the implant with a certain gap, and corresponds to the top end surface of the implant. The mounting plate and the nut simulate bone tissue. Loosening generally occurs at a threaded connection between the implant and the mounting plate. When the implant is loose, it will displace during the process of chewing. For example, the implant will rotate or shift around a loose part, changing a distance between the probe of the eddy current sensor 19 and the bottom surface of the implant. As a result, impedance of the eddy current sensor 19 will also be changed, thereby converting a displacement signal into an electrical signal.

A method for testing the fatigue strength of the implant with the above bionic oral cavity structure comprises steps of:

(1) calibrating, wherein a. when the movable platform is empty, setting a current position as an initial position, and moving vertically upwards from the initial position;

b. when the teeth of the upper jaw and lower jaw contact, stopping movable platform immediately, and recording a current displacement S1;

c. returning the movable platform to the initial position and putting a food sample on it;

d. carrying the food sample upwards with the movable platform until the food is in contact with the static platform, and recording a current displacement S2, wherein a thickness of the food sample is S1−S2; and e. resetting the platform;

(2) inputting preset parameters and modes of chewing operation, wherein the parameters comprise food compression ratio M, shear displacement coordinates, preset number of cycles N, etc.; and (3) cycling the chewing operation until a preset cycle ending condition is satisfied.

The mode of the chewing operation comprises compression chewing operation and/or shear chewing operation;

A cycle of the compression chewing operation comprises:

a. moving the movable platform vertically upwards with a displacement S2;

b. moving the movable platform vertically upwards with a displacement d, wherein d is (S1−S2)M; and c. moving the movable platform vertically downwards with a displacement d.

Before the shearing and chewing operations and cycling, a compression operation is also provided;

the compression operation specifically comprises:

a. moving the movable platform vertically upwards with a displacement S2; and b. moving the movable platform vertically upwards with a displacement d, wherein d is (S1−S2)M.

A cycle of the shearing and chewing operation specifically comprises:

a. moving the movable platform horizontally to (x, y); and b. moving the movable platform horizontally to (−x, −y).

The preset cycle ending condition may be any one of the follows:

a. reaching the preset number of cycles;

b. exceeding a preset stress threshold;

c. exceeding a preset sample looseness; and d. the sample is broken.

If at the end, the condition a is met while the conditions b, c, and d are not met, then the implant to be tested is qualified. In the process of testing the fatigue strength of the implant, if physical property changes of the food are not considered, then the stress detected by the flexible sensor is stable. However, after a certain number of detection cycles, the implant will break, and the stress will change suddenly and exceed a stable stress value. The stable stress value is obtained based on the first few cycles of recording, which can be an average value. The stress threshold is obtained by increase the average value by 5%-10% (other values can also be used, depending on material properties). When a measured stress value exceeds the preset stress threshold, the cycling ends and the implant is unqualified.

Sample break is different from sample fracture after a certain number of cycles. It usually occurs in the first cycle and is related to internal defects of the implant, such as cracks.

According to the present invention:

a circuit part of the flexible sensor is installed as follows: a signal output terminal of the flexible sensor is connected to an amplifying circuit; an analog signal conditioned by the amplifying circuit is sent to an A/D converter, and then is converted into a digital signal by the A/D converter; finally, the digital signal is transmitted to a computer for analyzing. An external signal line of the flexible sensor can be routed from the base of the gum;

A circuit part of the eddy current sensor is installed as follows: the eddy current sensor is connected to a proximitor, and the proximitor is connected to a power input terminal of the eddy current sensor. An output line is connected to an input port of a signal acquisition analyzer, and an output line of the signal acquisition analyzer is finally connected to a computer host.

What is claimed is:

1. A bionic oral cavity structure for testing, comprising: an upper jaw, a lower jaw, a drive unit, a sensor and a controller, wherein each of the upper jaw and the lower jaw comprises a tooth, a gum and a mounting plate; the tooth, the gum, and the mounting plate of the upper jaw are mounted on a static platform, and the static platform is mounted on a frame; the tooth, the gum, and the mounting plate of the lower jaw are installed on a movable platform, and the movable platform is connected to the drive unit, thereby moving up and down as well as left and right; the drive unit and the sensor are both electrically connected to the controller; wherein:

the gum is made of a soft elastic material, and a base of the gum has a through-hole drilled from top to bottom; a cap is formed by extending upward from a top opening of the through-hole; the tooth comprises a molar made of a hard material, and an implant; a top end of the implant passes through the through-hole of the gum and then extends into the cap; the gum and the implant are detachably mounted on the mounting plate; the sensor is a flexible sensor which covers the cap; the flexible sensor is provided with at least one sensing unit corresponding to a top portion of the cap and with at least two sensing units evenly distributed around a side portion of the cap; a bottom portion of the molar has a counterbore, and the molar is mounted on the gum; a structure constituted by the flexible sensor, the cap and the top end of the implant is integrally embedded in and tightly cooperate with the counterbore; the molar, the flexible sensor, the cap and the implant are arranged in sequence with no gap.

2. The bionic oral cavity structure, as recited in claim 1, wherein the gum is made of silica gel; in a non-testing state, the cap tightly cooperates with the molar and is in an elastic compression state; when an external force is applied, the cap is further compressed.

3. The bionic oral cavity structure, as recited in claim 1, wherein in a non-testing state, an internal side wall and a top wall of the counterbore are tightly attached to a non-sensing end of the flexible sensor; an external side wall and a top wall of the cap are tightly attached to a sensing end of the flexible sensor; and an internal side wall and an internal top wall of the cap are tightly attached to an external side wall and an external top wall of the top end of the implant.

4. The bionic oral cavity structure, as recited in claim 1, wherein the implant is screwed with the mounting plate and fastened by a nut.

5. The bionic oral cavity structure, as recited in claim 1, wherein a bottom end surface of the base is attached to the mounting plate, and the implant penetrates the mounting plate and the base from bottom to top.

6. The bionic oral cavity structure, as recited in claim 1, wherein the lower jaw is provided with a tongue, and the tongue is made of silica gel and mounted on the mounting plate.

7. The bionic oral cavity structure, as recited in claim 1, wherein the tooth of the upper jaw and the tooth of the lower jaw correspond to each other, and each of the upper jaw and the lower jaw is provided with an eddy current sensor; the eddy current sensor of the upper jaw part is installed directly above the implant with a certain gap, and the eddy current sensor of the lower jaw is installed directly below the implant with a certain gap.

8. The bionic oral cavity structure, as recited in claim 1, wherein three pairs of the drive units are evenly distributed around the movable platform; each of the drive units comprises a motor, a screw rod, a screw nut, a sliding block, a guide post, a connecting rod and a spherical hinge, wherein an output end of the motor is connected to the screw rod; two ends of the screw rod and two ends of the guide post are respectively supported on a support plate and are all arranged along a vertical direction; the screw nut is matched with the screw rod and fixedly connected to the sliding block; the sliding block cooperates with the guide post; two ends of the connecting rod are connected to the sliding block and the movable platform respectively through the spherical hinge; the motor and the support plate are mounted on the frame.

9. A method for testing physical properties of food comprising using the bionic oral cavity structure as recited in claim 1.

10. A method for testing denture fatigue comprising using the bionic oral cavity structure as recited in claim 1.

* * * * *